United States Patent [19]

Tsubota

[11] 4,350,588
[45] Sep. 21, 1982

[54] BIOLOGICAL FERMENTATION DEVICE

[76] Inventor: Junjiro Tsubota, 2392, Jindaiji-Machi, Chofu-shi, Tokyo 182, Japan

[21] Appl. No.: 177,878

[22] Filed: Aug. 14, 1980

[51] Int. Cl.³ .................................................. C02F 11/04
[52] U.S. Cl. ..................................... 210/208; 210/218; 210/255; 210/256; 210/197; 210/262; 210/603; 435/304; 435/307; 435/309; 435/315
[58] Field of Search ............... 210/177, 180, 183, 187, 210/207, 208, 256, 261, 255, 197, 260, 95, 218, 236–238, 603, 612, 613, 630; 435/304–308, 309, 310, 313, 314–316

[56] References Cited

U.S. PATENT DOCUMENTS 3,849,255 11/1974 Schlimme et al. ............... 435/304
3,923,652 12/1975 Condolios et al. ............... 210/208
4,048,019 9/1977 Numberger ....................... 435/304
4,163,720 8/1979 Mueller ............................. 210/197
4,165,285 8/1979 Wind et al. ....................... 210/197
4,256,837 3/1981 Fluri et al. ........................ 435/316

*Primary Examiner*—Benoit Castel
*Attorney, Agent, or Firm*—Shoemaker and Mattare, Ltd.

[57] ABSTRACT

Biological fermentation of organic matter is conducted in a single, unitary, integral vessel with both aerobic and anaerobic processes being conducted within that single vessel. Heat generated in the aerobic process is used to maintain the temperature of the anaerobic process at a desired level, and high molecular weight organic materials are reduced to matter having low molecular weight in that aerobic process. Low molecular weight material is transferred to a chamber in the vessel to be fermented in the anaerobic process.

34 Claims, 10 Drawing Figures

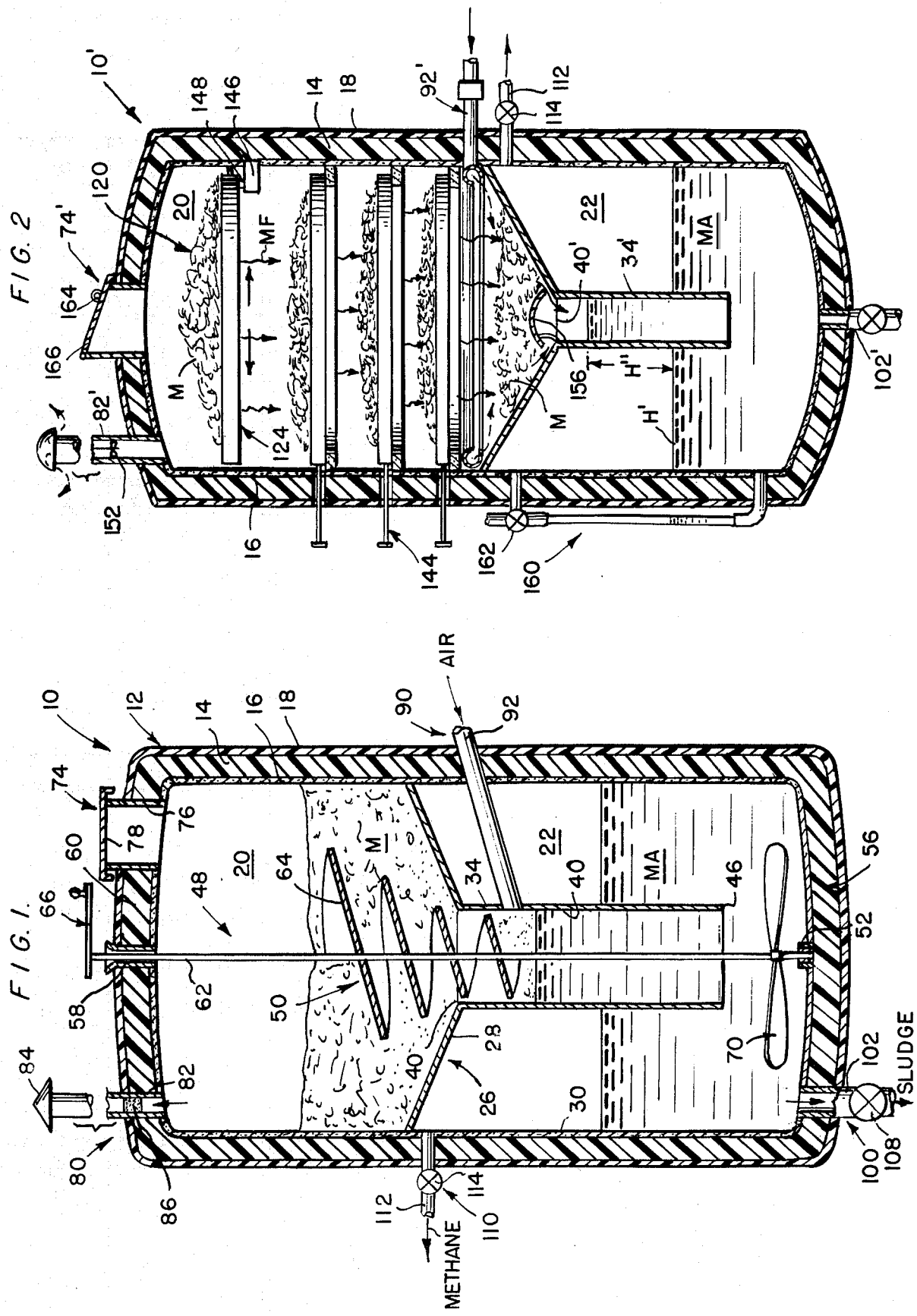

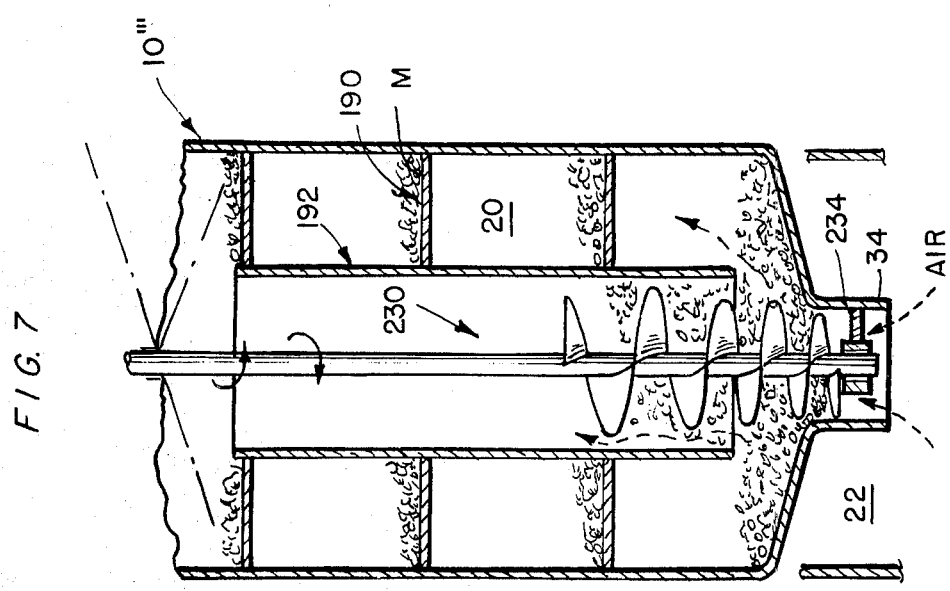
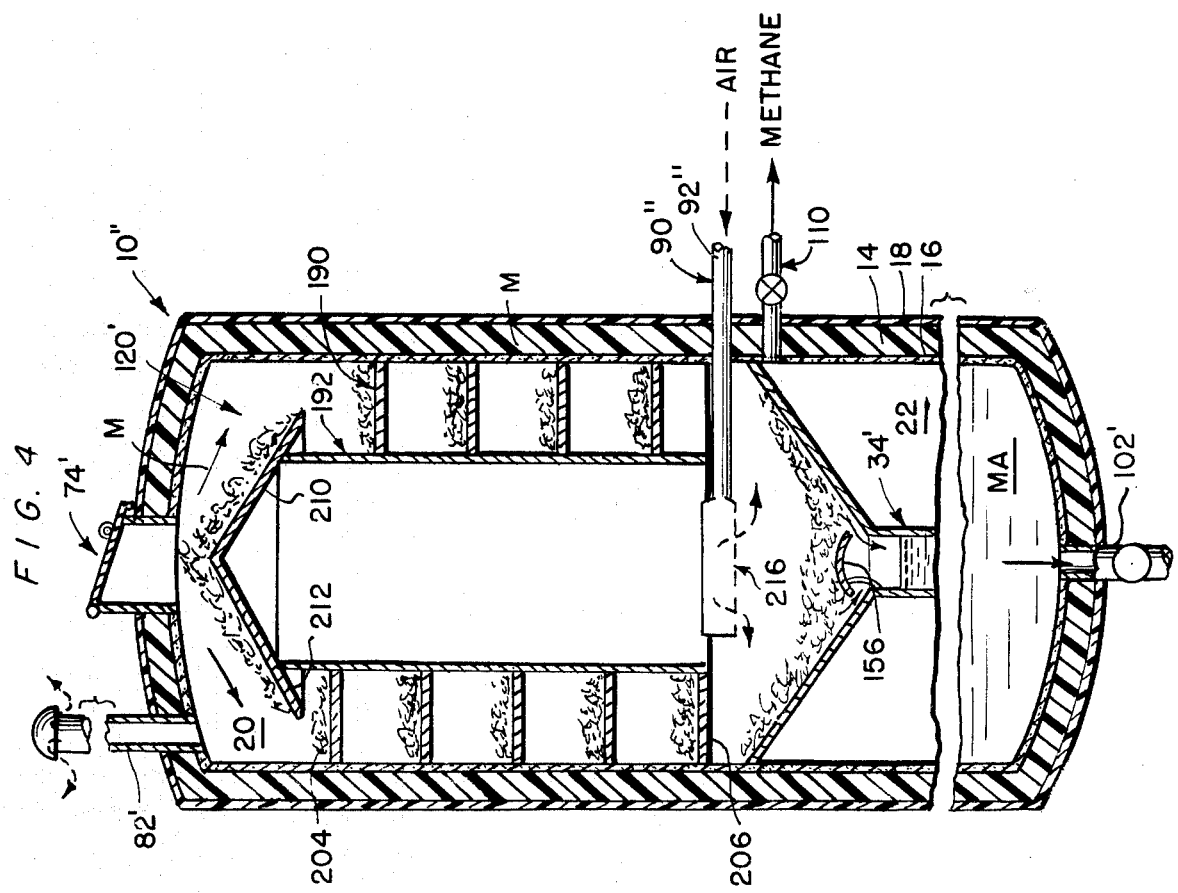

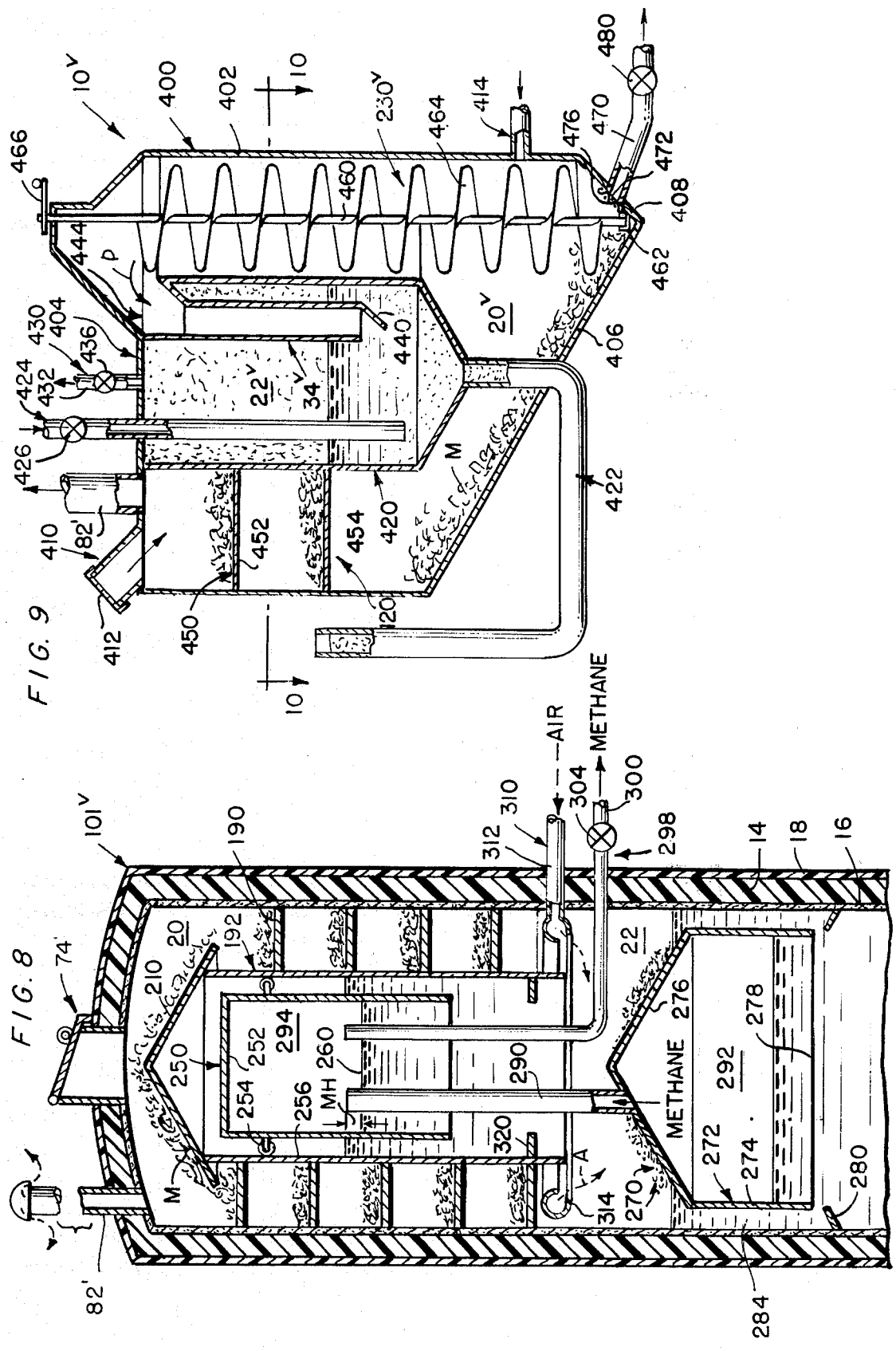

BIOLOGICAL FERMENTATION DEVICE

BACKGROUND OF THE INVENTION

The present invention relates in general to fermentation of materials, and, more particularly, to fermentation of organic materials.

Reduction of organic materials to sludge and the like has been successfully carried out in many countries, and such reduction is now being successfully carried out in countries such as India.

However, efficient anaerobic fermentation requires that the anaerobic process be carried out at between 30° C. and 40° C., and the organic material be of relatively low molecular weight.

Thus, if anaerobic fermentation is to be efficiently carried out on farms, or the like, there is need for warming the structure used if the farms, or the like, are located in cold regions, such as in the northern areas of the United States.

Furthermore, present fermentation methods require long periods of time in both the aerobic and anaerobic modes. Accordingly, there is need for a device and process which decreases the amount of time required to ferment material in both aerobic and anaerobic modes.

SUMMARY OF THE INVENTION

The device embodying the teachings of the present disclosure uses heat generated in an aerobic process to warm the structure in which an anaerobic process is carried out.

The device includes a single, unitary material containing vessel which is divided into an aerobic chamber and an anaerobic chamber with a material conveying means located to transfer lightweight material from the aerobic chamber to the anaerobic chamber.

The two chambers are in heat transferring contact with each other so that heat generated in the oxygen-fed aerobic chamber is transferred to the anaerobic chamber so the anaerobic process is carried out in a temperature range conducive to efficient anaerobic fermentation.

The vessel is preferably insulated and can be buried or not as suitable and can be of any suitable shape.

The temperature of the anaerobic chamber is held in a range of about 30° C. to 40° C. and low molecular weight material is transferred thereinto for efficient methane fermentation. The oxygen fed fermentation in the aerobic chamber is carried out at about 60° C. to 80° C. and reduces high molecular weight material to low molecular weight material which is transferred to the anaerobic chamber for anaerobic fermentation. The heat generated in the aerobic chamber is used to warm the anaerobic chamber to the proper temperature for efficient anaerobic fermentation.

The device disclosed herein reduces the time to ferment materials from the two months now required for aerobic fermentation to six to eight days; and the time required for anaerobic fermentation from about one week to one to two days. It is noted that using the teachings of the present disclosure, one ton of organic material can produce 824 cubic feet of methane. The methane can be used in any suitable manner.

The device of the present disclosure uses common material such as household, or agricultural and animal waste, seaweed, or the like.

OBJECTS OF THE INVENTION

It is a main object of the present invention to carry out both aerobic and anaerobic fermentation of organic material in a single, unitary, integral vessel.

It is another object of the present invention to use heat generated in an aerobic fermentation process to warm an anaerobic fermentation process to a proper temperature range.

It is a further object of the present invention to use an aerobic fermentation process to reduce organic material to a material having a molecular weight proper for efficient anaerobic fermentation.

These together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 1 is an elevation view of a first form of the device embodying the teachings of the present invention.

FIG. 2 is an elevation view of a second form of the device embodying the teachings of the present invention.

FIG. 4 is an elevation view of a third form of a device embodying the teachings of the present invention.

FIG. 7 is an elevation view of a forth form of the device embodying the teachings of the present invention.

FIG. 8 is an elevation view of a fifth form of the device embodying the teachings of the present invention.

FIG. 9 is an elevation view of a sixth form of the device embodying the teachings of the present invention.

DETAILED DESCRIPTION OF THE INVENTION

Figure 3:
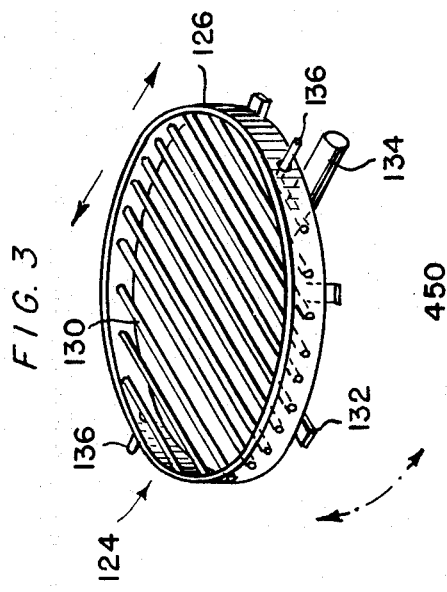
FIG. 3 is a perspective of a grill unit used in the second form of the device shown in FIG. 2.

Shown in FIG. 1 is a vessel 10 for biologically fermenting material both aerobically and anaerobically. The vessel is integral and unitary and includes a casing 12 comprised of a layer of insulating material 14 sandwiched between an inner layer 16 and an outer layer 18. Preferably, the layer 16 includes fiber reinforced concrete; however, other materials can be used if suitable. The vessel 10 is shown in FIG. 1 as being cylindrical, but other vessel shapes can be used without departing from the scope of the present disclosure.

The vessel is divided into an aerobic chamber 20 and an anaerobic chamber 22 by a partition 26 which has a conical wall 28 sealed at the outer rim thereof to inner surface 30 of the casing and a downcomer pipe 34 integrally attached to the apex of the wall 28 to depend into the anaerobic chamber. The conical wall 28 is sloped toward the anaerobic chamber so that organic material M supported on upper surface 36 in the aerobic chamber is gravity biased toward port 40 which fluidly connects the aerobic chamber with bore 42 of the downcomer pipe. The downcomer pipe has lower end 46 thereof in fluid communication with the anaerobic chamber so that, when desired, the aerobic chamber and the anaerobic chamber can be placed in fluid communication with each other via the downcomer pipe 34. The partition thus acts as a hopper for material M which is eventually fermented and fed to the anaerobic chamber. The materials and dimensions thereof used for the partitions disclosed herein are selected according to the temperature expected in the aerobic chamber so that the proper amount of heat is transferred to the anaerobic chamber so that the anaerobic process is carried out in the proper temperature range, e.g., 30° C. to 40° C. Insulation can be added to the partition if necessary.

A material conveyor 48 includes an auger 50 which is positioned along the longitudinal centerline of the vessel 10 and includes a step bearing 52 mounted on the casing bottom wall 56 and a guide bearing 58 mounted on casing top wall 60. An operating shaft 62 is rotatably supported in the step bearing and extends through the guide bearing. A screw conveyor 64 is in the shape of an Archimedes' spiral and is mounted on the operating shaft for rotation therewith. A crank 66 is attached to the shaft to rotate that shaft either manually or automatically by a motor (not shown).

The radially decreasing size of the screw conveyor permits conveying of material into the downcomer pipe when the shaft is rotated in one direction, and the comingling of material when the shaft is rotated in the other direction. For example, when the conveyor is rotated clockwise, material having low molecular weight moves downwardly into the downcomer pipe, and when the conveyor is rotated counterclockwise, the material is comingled. The function and result of such operation will be apparent from the ensuing discussion.

A paddle 70 is shown in FIG. 1 as being mounted on the shaft for rotation therewith. The paddle is mounted on the shaft to be located in the anaerobic chamber to mix material MA located in that chamber 22. It is noted that the paddle is not required.

A material inlet 74 includes a tube 76 mounted on the vessel top wall and a cap 78 covering that tube. Organic material to be fermented in the vessel is placed therein via the inlet 74.

A vent 80 includes a vent pipe 82 mounted in the vessel top wall and a vent cap 84 covering that pipe. A filter 86 is located in the pipe 82.

An air inlet 90 includes an air conduit 92 fluidly connected at one end thereof to the downcomer pipe and at the other end thereof to an air source (not shown). The conduit extends through the vessel wall at an angle to the horizontal, and air from this conduit moves into the aerobic chamber.

A sludge removal system 100 includes a sludge conduit 102 connected to the vessel bottom 56 to be in fluid communication with the anaerobic chamber to remove sludge therefrom to a sludge collection means (not shown). A control valve 108 is located in the sludge conduit to control flow therethrough.

A gas bleed system 110 for venting methane gas produced by the anaerobic fermentation process includes a conduit 112 mounted in the vessel wall to be in fluid communication with the anaerobic chamber and with a methane storage means (not shown). A control valve 114, which may be hand or automatically operated, is located in the conduit.

Material M is subject to aerobic fermentation in the chamber 20 wherein the high molecular weight materials are broken down and heat is produced. The aerobic fermentation process generally occurs at about 60° C. to 80° C., and thus produces heat which will be transferred to the anaerobic chamber which is at a temperature of about 30° C. to 40° C. The low molecular weight materials and separated water are conveyed into the anaerobic chamber 22 by the auger and the heat generated in the aerobic chamber is transferred to the anaerobic chamber via the partition. The material MA in the anaerobic chamber is heated to a temperature suitable for conducting anaerobic fermentation by the heat generated in the aerobic chamber, and the material having the proper molecular weight is located in the chamber 22. Thus, efficient anaerobic fermentation occurs in the chamber 22 and produces sludge which is removed by the system 100.

Air is added via the inlet 90 and overpressure in chamber 20 is prevented by the vent 80 and in chamber 22 by the bleed system 110. Air and separated water are vented from the vent 80. The valve 114 is opened and the head H established in the downcomer pipe forces methane out of the chamber 22. The insulated vessel assures proper fermentation temperatures, even in cold environmental conditions such as may occur in winter nights in the northern United States. It is also noted that air removed via the vent 80 also removes some separated water from the aerobic chamber. The amount of water in the material in chamber 20 drops from 80%–90% to 50%–60%, which is an ideal percentage for the fermentation process occurring in chamber 20.

The partition wall is sealed to the vessel inner surface in an airtight manner.

Preferably, the insulation is fiberglass, however, other forms of insulation can be used if suitable.

Thus, continuous fermentation occurs in the vessel 10 with the aerobic fermentation occurring in chamber 20 breaking down the material and generating sufficient heat so that anaerobic fermentation can occur efficiently in chamber 22.

An alternative form of the vessel 10 is shown in FIG. 2 as vessel 10'. The vessel 10' includes a cascade system 120 in place of the auger 50. The cascade system includes a plurality of vertically spaced gratings 124, one of which is shown in FIG. 3 to include a tubular wall 126 to which is attached a plurality of bars 130, mounting pads 132, shaft 134 and stub shaft 136. The bars are spaced apart to permit material to fall through the grillwork as indicated in FIG. 2 by arrows MF.

As shown in FIG. 2, the gratings are supported on mounts 140 which are affixed to the vessel inner surface and have the spacing between the bars 130 selected to appropriately filter the material passing therethrough. The number and grill size of the grates is selected to pass the appropriate material.

The grates are vibrated either by hand, via hand operated cranks 144, or by a motor 146 and motor shaft 148.

The vessel 10' differs from the vessel 10 to accommodate the cascade system. Thus, vessel 10' includes a sludge pipe 102' and a material inlet 74' located along the longitudinal centerline thereof, and an annular air inlet pipe 92' is included in place of the air inlet pipe 92 in the vessel 10. Furthermore, a fan 152 is located in the vent pipe 82' to assist removal of air from the aerobic chamber of the vessel 10'. A downcome pipe cap 156 is mounted to partially occlude the port 40' of the downcomer pipe 34', and a pressure guage 160 includes a valve 162 which is operated to determine the liquid level H' in the anaerobic chamber or the liquid level H'' in the downcomer pipe 34' as desired. As shown in FIG. 2, the material inlet pipe 74' has a slanted top with a handle 164 on cap 166 thereof.

Operation of the vessel 10' is similar to that of the vessel 10, wherein the aerobic fermentation breaks down the molecules of the material and supplies heat to the anaerobic process along with material having a molecular weight which is proper for efficient anaerobic fermentation.

Figure 5:
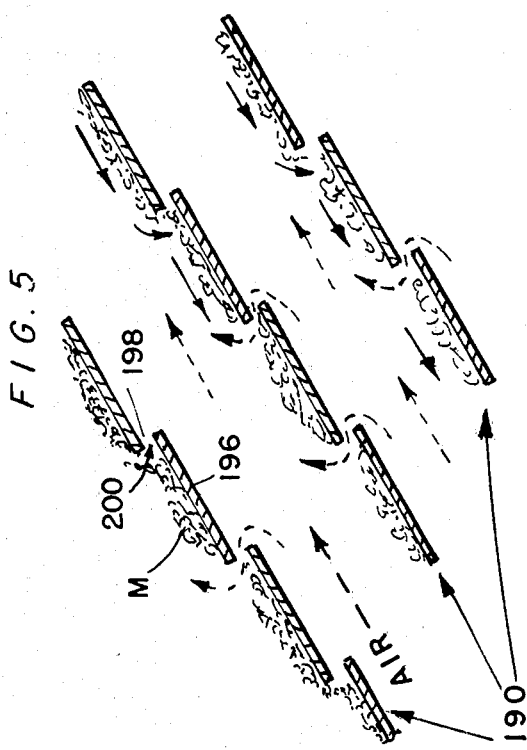
FIG. 5 is an elevation view of a set of flumes used with the device embodying the teachings of the present invention.
Figure 6:
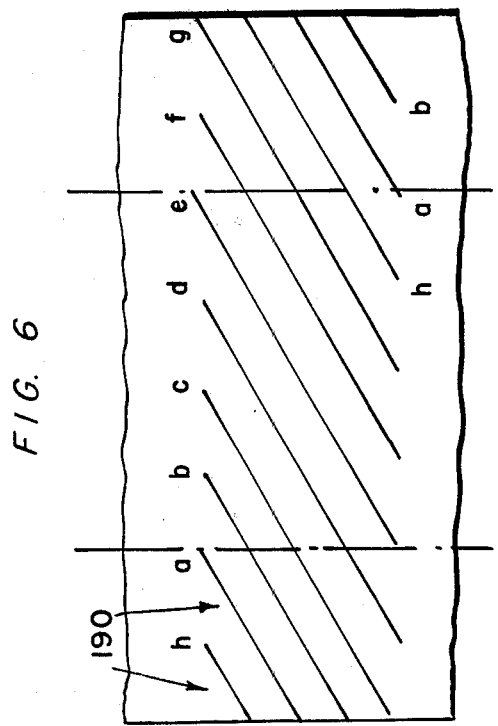
FIG. 6 is a schematic of a setup of flumes used with the device embodying the teachings of the present invention.

Shown in FIG. 4 is another form of the fermentation vessel and is denoted as vessel 10'', which includes a cascade system 120' having a helical flume 190 surrounding a central housing 192 mounted centrally of the vessel. The helical flume is best shown in FIG. 5 to include a plurality of planar segments 196 which are downwardly sloped and spaced apart to define slots 198 therebetween to define steps 200. The cascade system can include one flume, or a plurality of flumes as shown in FIGS. 5 and 6, with FIG. 4 showing one flume. The flumes are sloped to cause material M to slide down the flume and be agitated as the downward slide continues. The material tumbles down the steps to be upset and further agitated thereby. Air flows up the flumes and through the slots to heat and dry the material.

Ideally, the uppermost portion 204 of each flume is at an angle of about 30° with respect to the horizontal, and slopes into the plane of the paper in FIG. 4, and the angle of the flume increases uniformly so that the lowermost portion 206 of that flume is at an angle of about 40° with respect to the horizontal.

The inner housing includes a roof 210 which is sloped at about 30° with respect to the horizontal at overhang 212 thereof.

An air inlet 90'' includes a horizontally disposed inlet pipe 32'' and an air ejector 216 located beneath the housing 192. Otherwise, vessel 10'' is similar to the vessel 10', and operates similarly to aerobically permit material M as that material slides down the flume or flumes and then flows into the anaerobic chamber via the downcomer pipe. Again, the high molecular weight products are separated in the aerobic chamber and the generated heat is used to warm the anaerobic chamber to a proper temperature to efficiently carry out anaerobic fermentation.

A vessel 10''' is shown in FIG. 7 wherein an auger 230 is positioned in the central housing 192. The auger 230 is supported by a guide bearing 234 located in the downcomer pipe and extends thereinto. Material falling into the downcomer pipe from the flumes is further agitated and separated by the auger to further insure proper separation of the high molecular weight material prior to the material having the proper molecular weight entering the anaerobic chamber via the downcomer pipe.

A vessel $10^{IV}$ is shown in FIG. 8 to includes a gas container system 250 in the central housing 192. The gas container system includes a tubular container 252 mounted in the housing 192 to be vertically movable therein. Guide wheels 254 are mounted on the container 252 and contact inner surface 256 of the housing. Fluid 260, such as water, or the like, is contained in the housing, and the container has an open bottom which permits this fluid to flow into and out of the container according to the pressure within the container 252. The pressure within the container 252 also sets the vertical position of that container within the housing.

A partition 270 separates the aerobic and anaerobic chambers. The partition includes a housing 272 having a wall 274 and a sloped roof 276 with an open bottom 278. An annular block 280 is located on the vessel wall subjacent the housing wall 274, and an annular gap 284 is defined between the housing wall 274 and the vessel wall.

A conduit 290 establishes fluid communication between interior 292 of the housing 272 and interior 294 of the gas container 252 so that methane gas generated in the anaerobic chamber is conducted into the container 252. A methane vent system 298 includes a methane conduit 300 fluidly connected at one end thereof to the container interior 292 and at the other end thereof to a methane gas storage or disposal means (not shown). A control valve 304 is included in the pipe 300.

An air inlet system 310 includes an air conduit 312 connected at one end thereof to a source of air (not shown) and at the other end thereof to an annular air dispenser pipe 314 which surrounds the central housing and ingests air into the aerobic chamber as indicated in FIG. 8 by arrows A.

A limit stop 320 is mounted on the central housing to limit the amount of downward movement permitted for the gas container.

As can be seen from FIG. 8, the gas generated in the anaerobic chamber is vented into the gas container and a head MH is established in the fluid 260 contained in that chamber. The gas container moves according to the heat and at suitable times, the gas stored in that container can be vented for use when ambient temperature drops, or disposal as suitable.

The angle of the flume 190 and the angle of the roof 210 in the vessel $10^{IV}$ are similar to those angles in the vessel 10''', and the angle between the roof 210 and the horizontal is preferably 40° as indicated in FIG. 8.

Material M exiting the cascade system falls onto the roof 276 and falls into the gap 284 which serves as the downcomer between the aerobic and the anaerobic chambers of the vessel $10^{IV}$. The sediment block 280 prevents some of the gas generated in the anaerobic chamber from flowing up the annular gap and thereby bypassing the just-described gas container system.

Figure 10:
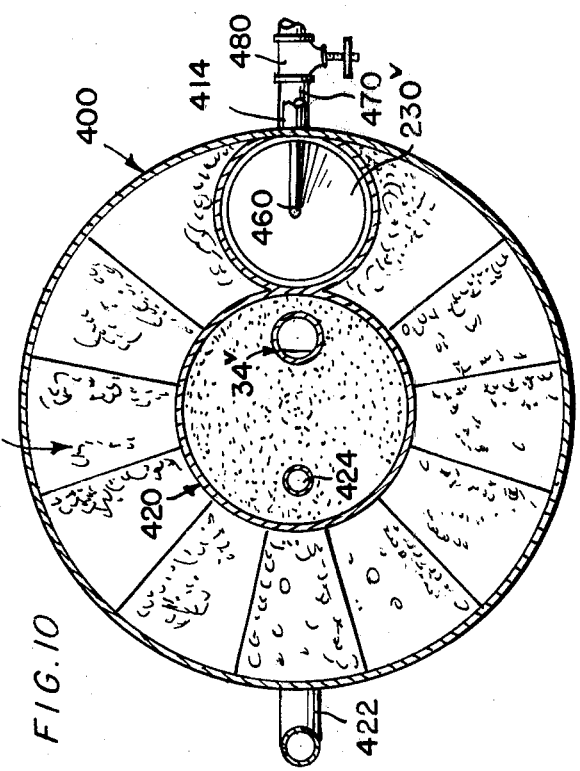
FIG. 10 is a view taken along line 10—10 of FIG. 9.

A vessel $10^{V}$ is shown in FIGS. 9 and 10 and includes an outer housing 400 having a side wall 402, a top 404 and a bottom composed of sloped walls 406 and 408. The housing 400 can be insulated as above-discussed, if so desired. A material inlet pipe 410 includes a cap 412 and an air inlet pipe 414 is mounted on the wall 402.

The anaerobic chamber $22^{V}$ of the vessel $10^{V}$ includes a housing 420 depending from the vessel top wall and a sludge removal conduit 422 removes sludge from this housing 420 to be disposed of as desired.

A water inlet system includes a water conduit 424 fluidly connected to the anaerobic chamber $22^{V}$. A flow control valve 426 is mounted in the conduit 424. A gas outlet system 430 includes a gas conduit 432 fluidly connecting the anaerobic chamber to a gas storage or disposal means (not shown) and having a flow control valve 436 thereon.

The aerobic chamber $20^{V}$ of the vessel $10^{V}$ surrounds the housing 420 and includes a cascade system $120^{V}$ and a material conveying auger $230^{V}$. A downcomer pipe $34^{V}$ connects the aerobic and anaerobic chambers together and a weir 440 on one end thereof to deflect the material into the housing 420 from the downcomer pipe and to act as a baffle for at least partially preventing gas generated in the anaerobic chamber from flowing up the downcomer pipe. An entrance threshold 444 connects the downcomer pipe to the aerobic chamber adjacent the auger upper end.

As shown in FIGS. 9 and 10, the cascade system 120$^V$ includes a helical flume 450 which partially surrounds the housing 420 and connects the material inlet 410 with the bottom of the vessel adjacent the auger lower end. The flume 450 is similar to the flume discussed above and has an angle at upper end 452 of about 30° and an angle at lower end 454 of about 40° with respect to the horizontal. The wall 406 has an angle of about 40° with respect to the horizontal and material exiting the flume flows over this wall to the auger lower end. The auger lifts this material up to the threshold of the downcomer and deposits that material therein for transfer to the aerobic chamber 22$^V$.

As shown in FIG. 9, the auger includes an operating shaft 460 mounted at the upper end thereof in a step bearing 462 and mounted near the upper end thereof in the vessel top wall. The auger includes a screw blade 464 and a crank 466 for rotating same. Material follows a path indicated in FIG. 9 by the arrow D. A motor (not shown) can be used to rotate the material conveyor if so desired.

A conduit 470 is fluidly connected to the aerobic chamber by a port 472 to conduct separated water out of the aerobic chamber. A filter 476 covers the port 472 to prevent material M from flowing into the conduit 470. The conduit is fluidly connected to a water storage or reuse means (not shown) and includes a control valve 480 therein.

The vessel 10$^V$ operates in a manner similar to the other vessels whereby heat generated in the aerobic chamber is used to warm the anaerobic chamber to a proper temperature, and only material having the proper molecular weight is transferred to the anaerobic chamber for processing therein. Water, gas and sludge are removed from the anaerobic chamber by the appropriate conduits as shown in FIG. 9 and as discussed above.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A device for conducting fermentation of materials comprising:

a unitary insulated vessel having an inlet for organic material to be fermented;

a partition mounted in said vessel dividing said vessel into an aerobic fermentation chamber and an anaerobic fermentation chamber, said partition including a conical portion and a downcomer means, said aerobic chamber being in fluid communication with said inlet and said anaerobic chamber, said partition supporting the organic material and being constructed of material capable of transferring heat from said aerobic chamber to said anaerobic chamber in quantities sufficient so that an anaerobic fermentation process conducted in said anaerobic chamber occurs at a desired temperature;

material separating means in said aerobic chamber separating material in said aerobic chamber into high and low molecular weight groups;

air ingesting means fluidly connected to said aerobic chamber;

material transfer means mounted in said vessel to transfer said low molecular weight material from said aerobic chamber to said anaerobic chamber while retaining said high molecular weight material in said aerobic chamber so that anaerobic fermentation occurs with the low molecular weight material;

gas bleed means fluidly connected to said anaerobic chamber;

a gas vent means fluidly connected to said aerobic chamber; and sludge removal means connected to said anaerobic chamber.

2. The device defined in claim 1 wherein said vessel includes a layer of insulation sandwiched between an inner and an outer layer.

3. The device defined in claim 1 further including a sight gauge on said vessel for determining the level of liquid located in said anaerobic chamber.

4. The device defined in claim 3 wherein said sight gauge includes a valve so that said sight gauge can also be used for determining the level of liquid located in said downcomer means.

5. The device defined in claim 1 wherein said anaerobic chamber is located within said aerobic chamber.

6. The device defined in claim 5 wherein said material transfer means includes an arcuate flume means located in said aerobic chamber.

7. The device defined in claim 6 further including a water bleed means fluidly connected to said aerobic chamber.

8. The device defined in claim 6 wherein said vessel includes a sloped wall onto which material from said flume means falls.

9. The device defined in claim 8 wherein said vessel sloped wall slopes at an angle of about 40° with respect to horizontal.

10. The device defined in claim 6 wherein said flume means forms an angle of about 30° with respect to horizontal near the top thereof and an angle of about 40° near the bottom thereof.

11. The device defined in claim 10 wherein said flume means includes a plurality of steps.

12. The device defined in claim 11 wherein said flume means includes a plurality of path forming chutes which are vertically spaced apart.

13. A device for conducting fermentation of material comprising:

a unitary insulated vessel having an inlet for organic material to be fermented;

a partition mounted in said vessel dividing said vessel into an aerobic fermentation chamber and an anaerobic fermentation chamber, said aerobic chamber being in fluid communication with said inlet and said anaerobic chamber, said partition supporting the organic material and being constructed of material capable of transferring heat from said aerobic chamber to said anaerobic chamber in quantities sufficient so that an anaerobic fermentation process conducted in said anaerobic chamber occurs at a desired temperature;

material separating means in said aerobic chamber separating material in said aerobic chamber into high and low molecular weight groups;

air ingesting means fluidly connected to said aerobic chamber;

an auger material transfer means mounted in said vessel to transfer said low molecular weight material from said aerobic chamber to said anaerobic chamber while retaining said high molecular weight material in said aerobic chamber so that anaerobic fermentation occurs with the low molecular weight material;

gas bleed means fluidly connected to said anaerobic chamber;

a gas vent means fluidly connected to said aerobic chamber; and sludge removal means connected to said anaerobic chamber.

14. The device defined in claim 13 wherein said auger includes a screw conveyor.

15. The device defined in claim 14 wherein said screw conveyor is in the shape of an Archimedes' spiral.

16. The device defined in claim 15 further including a paddle mounted on said auger to be located in said anaerobic chamber.

17. The device defined in claim 13 wherein said auger includes a hand crank thereon.

18. A device for conducting fermentation of materials comprising:

a unitary insulated vessel having an inlet for organic material to be fermented;

a partition mounted in said vessel dividing said vessel into an aerobic fermentation chamber and an anaerobic fermentation chamber, said aerobic chamber being in fluid communication with said inlet and said anaerobic chamber, said partition supporting the organic material and being constructed of material capable of transferring heat from said aerobic chamber to said anaerobic chamber in quantities sufficient so that an anaerobic fermentation process conducted in said anaerobic chamber occurs at a desired temperature;

material separating means in said aerobic chamber separating material in said aerobic chamber into high and low molecular weight groups;

air ingesting means fluidly connected to said aerobic chamber;

a cascade material transfer means mounted in said vessel to transfer said low molecular weight material from said aerobic chamber to said anaerobic chamber while retaining said high molecular weight material in said aerobic chamber so that anaerobic fermentation occurs with the low molecular weight material;

gas bleed means fluidly connected to said anaerobic chamber;

a gas vent means fluidly connected to said aerobic chamber; and sludge removal means connected to said anaerobic chamber.

19. The device defined in claim 18 wherein said cascade means includes a plurality of gratings.

20. The device defined in claim 19 wherein at least one of said gratings includes a vibrator means.

21. The device defined in claim 20 wherein said vibrator means includes a motor.

22. The device defined in claim 20 wherein said vibrator means includes a hand crank.

23. A device for conducting fermentation of materials comprising:

a unitary insulated vessel having an inlet for organic material to be fermented;

a partition mounted in said vessel dividing said vessel into an aerobic fermentation chamber and an anaerobic fermentation chamber, said aerobic chamber being in fluid communication with said inlet and said anaerobic chamber, said partition supporting the organic material and being constructed of material capable of transferring heat from said aerobic chamber to said anaerobic chamber in quantities sufficient so that an anaerobic fermentation process conducted in said anaerobic chamber occurs at a desired temperature;

material separating means in said aerobic chamber separating material in said aerobic chamber into high and low molecular weight groups;

air ingesting means fluidly connected to said aerobic chamber;

a helical flume material transfer means mounted in said aerobic chamber to transfer said low molecular weight material from said aerobic chamber to said anaerobic chamber while retaining said high molecular weight material in said aerobic chamber so that anaerobic fermentation occurs with the low molecular weight material;

gas bleed means fluidly connected to said anaerobic chamber;

a gas vent means fluidly connected to said aerobic chamber; and sludge removal means connected to said anaerobic chamber.

24. The device defined in claim 23 wherein said flume means forms an angle of about 30° with respect to horizontal near the top thereof and an angle of about 40° near the bottom thereof.

25. The device defined in claim 24 wherein said flume means includes a plurality of steps.

26. The device defined in claim 25 wherein said flume means includes a plurality of path forming chutes which are vertically spaced apart.

27. The device defined in claim 23 further including a central housing mounted in said vessel and within said flume means.

28. The device defined in claim 27 further including an auger located within said central housing.

29. The device defined in claim 27 further including a gas container movably mounted within said central housing.

30. The device defined in claim 29 further including a second housing located in said anaerobic chamber.

31. The device defined in claim 30 further including conduit means fluidly connecting said second housing to said gas container.

32. The device defined in claim 31 further including another gas bleed means fluidly connected to said gas container.

33. The device defined in claim 30 further including an annular blocking means mounted on said vessel to be subjacent said second housing and to be circumambient said second housing.

34. The device defined in claim 29 further including guide wheels on said gas container and a stop means on said central housing for limiting the movement of said gas container.

* * * * *